Figure 1:
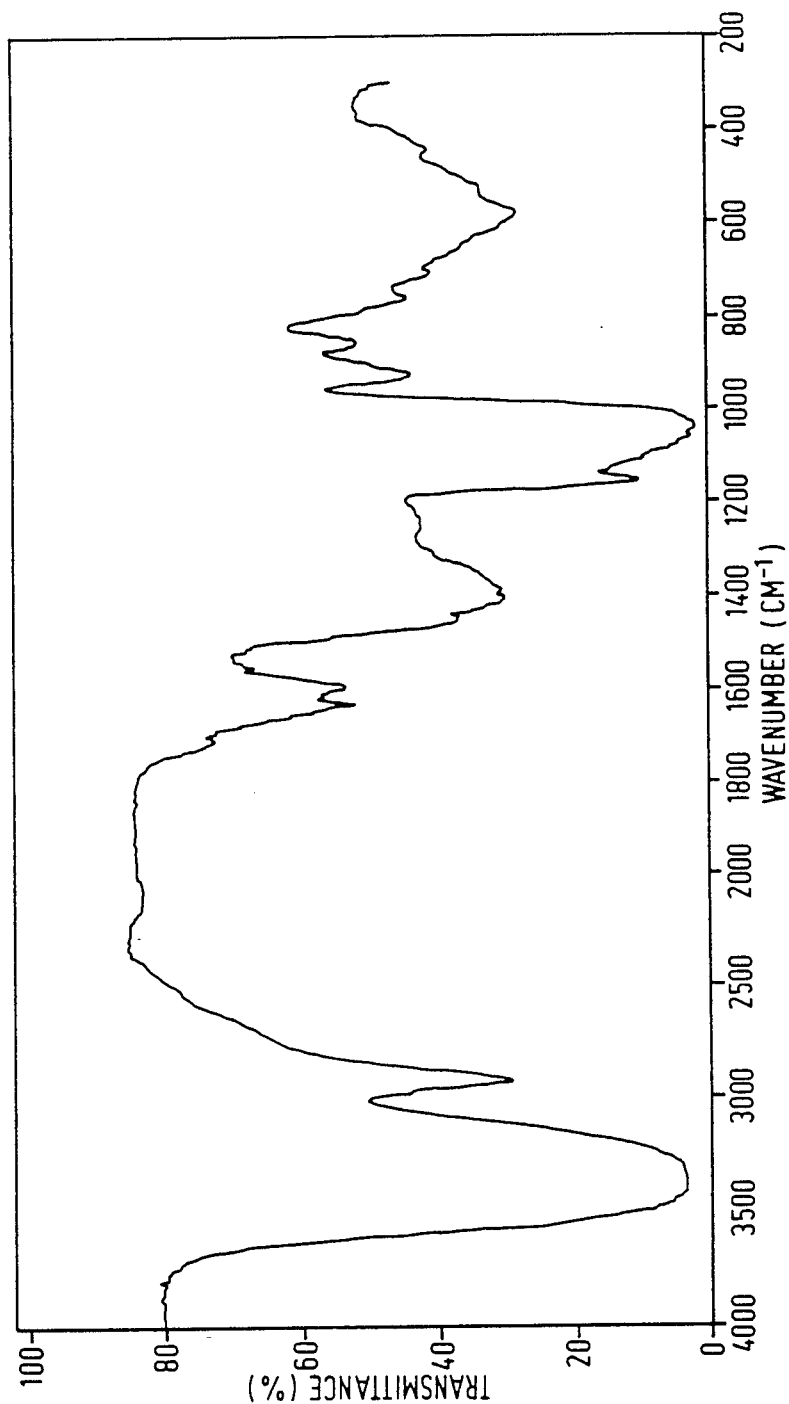

United States Patent [19]

Vértesy et al.

[11] Patent Number: 4,632,917
[45] Date of Patent: Dec. 30, 1986

[54] PSEUDOOLIGOSACCHARIDES WITH AN α-GLUCOSIDASE-INHIBITING ACTION, THEIR USE AND PHARMACEUTICAL PRODUCTS

[75] Inventors: László Vértesy, Eppstein; Rudolf Bender, Kronberg; Hans-Wolfram Fehlhaber, Idstein; Karl Geisen, Frankfurt am Main, all of Fed. Rep. of Germany

[73] Assignee: Hoechst Aktiengesellschaft, Fed. Rep. of Germany

[21] Appl. No.: 771,610

[22] Filed: Sep. 3, 1985

[30] Foreign Application Priority Data

Sep. 4, 1984 [DE] Fed. Rep. of Germany ....... 3432431

[51] Int. Cl.$^4$ ...................... A61K 31/73; C08B 37/00
[52] U.S. Cl. ......................................... 514/54; 424/49; 514/835; 514/866; 536/18.7; 536/123
[58] Field of Search .......................... 514/54, 835, 866; 536/18.7; 424/49

[56] References Cited

U.S. PATENT DOCUMENTS

| | | | |
|---|---|---|---|
| 4,062,950 | 12/1977 | Frommer et al. | 536/18.7 |
| 4,065,557 | 12/1977 | Frommer et al. | 536/18.7 |
| 4,254,256 | 3/1981 | Otani et al. | 536/18.7 |

Primary Examiner—Johnnie R. Brown
Attorney, Agent, or Firm—Finnegan, Henderson, Farabow, Garrett & Dunner

[57] ABSTRACT

Pseudooligosaccharides of the formula I

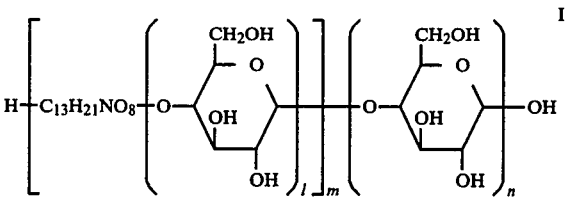

in which l, m and n have the meanings given, physiologically acceptable salts thereof with acids, a process for their preparation, pharmaceutical products and their use are described. The compounds have an α-glucosidase-inhibiting action.

7 Claims, 2 Drawing Figures

PSEUDOOLIGOSACCHARIDES WITH AN α-GLUCOSIDASE-INHIBITING ACTION, THEIR USE AND PHARMACEUTICAL PRODUCTS

The invention relates to novel biologically active pseudooligosaccharides and their physiologically acceptable salts. They have α-glucosidase-inhibiting properties, i.e., for example, α-amylase- and disaccharidase-inhibiting properties, and can therefore be used in human medicine and animal medicine, in animal nutrition and in starch biotechnology.

The pseudooligosaccharides according to the invention have the following general formula I.

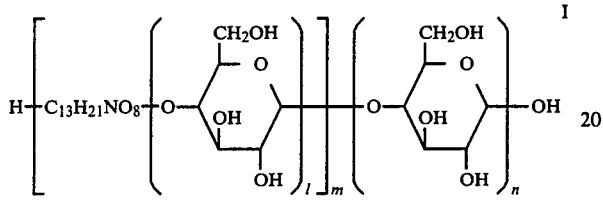

in which
l = 1 or 2
m = 1, 2 or 3 and
n denotes an integer from 1 to 20.
They have a basic character and reducing properties.

The invention particularly relates to the pseudooligosaccharides of the formula I wherein l denotes 1, m denotes 1 or 2 and n denotes 1, 2, 3 or 4. Particularly preferred compounds of the formula I are those in which l is 1, m is 2 and n is 1: $C_{44}H_{74}N_2O_{32}$;
molecular weight 1,142 (W-46 A);
l is 1, m is 2 and n is 2: $C_{50}H_{84}N_2O_{37}$;
molecular weight 1,304 (W-46 B);
l is 1, m is 2 and n is 3: $C_{56}H_{94}N_2O_{42}$;
molecular weight 1,466 (W-46 C)
and physiologically acceptable salts thereof with acids. The pseudooligosaccharides of the formula I are also called the inhibitors W-46 and W-46 A, B and C below. The compounds are isolated either as a mixture or as individual compounds.

The invention furthermore relates to a process for the preparation of the pseudooligosaccharides of the formula I, pharmaceutical products containing compounds of the formula I and their use as a medicament, diagnostic aid and reagent.

The invention particularly relates to a process for the preparation of the inhibitors W-46 A, B and C, pharmaceutical products containing these compounds and their use as a medicament, diagnostic aid and reagent.

The process for the preparation of the pseudooligosaccharides of the formula I comprises culturing, in a fermentation medium by the submerged method, Streptomycetes which produce a pseudooligosaccharide of the formula I, isolating the inhibitors from the mycelium or the culture filtrate in a manner which is known per se and purifying them. Of the Streptomycetes, *Streptomyces galbus* subsp. FH 1716 is suitable. This strain has been deposited at the Deutsche Sammlung von Mikroorganismen (DSM) (German Collection of Microorganisms) under the registration No. DSM 3007. The variants and mutants of this strain, however, can also be used for obtaining the W-46 inhibitors.

The taxonomic properties of Streptomyces galbus subsp. FH 1716, DSM 3007 correspond to the description of *Streptomyces galbus* according to Bergey's Manual of Determinative Bacteriology, 8th edition, publisher: Williams & Wilkins Corp. Baltimore, 1974. Differences from the strains described exist in some physiological features. *Streptomyces galbus* DSM 40480 has been chosen here as a comparison and reference strain, and the features are compared in the following Table 1.

TABLE 1

| | Carbon utilization * of the strains | |
|---|---|---|
| | I | II |
| | Str. galbus FH 1716 | Str. galbus DSM 40480 |
| Arabinose | + | (+) |
| Xylose | (+) | + |
| Rhamnose | − | − |
| Raffinose | − | (+) |
| Mannose | + | + |
| Inositol | − | + |
| Starch | − | (+) |
| p-Hydroxybenzoic acid | (+) | + |
| Oxalate | (+) | − |
| Malonate | − | (+) |
| Lactate | − | (+) |
| Gluconate | − | (+) |

* +: good utilization, (+): questionable utilization, −: no utilization

*Streptomyces galbus* strains with the physiological features of column I as shown in Table 1 have not yet been described in the literature. The strain *Streptomyces galbus* subsp. FH 1716, DSM 3007 is consequently novel. The invention therefore also relates to *Streptomyces galbus* FH 1716, DSM 3007.

The W-46 inhibitors are advantageously obtained by the following procedure:

*Streptomyces galbus* FH 1716 is cultured in an aqueous nutrient medium under submerged and preferably aerobic conditions until an adequate concentration of the W-46 inhibitors is obtained. The nutrient medium contains on the one hand sources of carbon, such as, for example, carbohydrates, and on the other hand sources of nitrogen, which include suitable nitrogen compounds, such as, for example, protein-containing materials. Preferred compounds which supply carbon are glucose, sucrose, glycerol, malt extract, starch, oils, fats and the like. Preferred substances which supply nitrogen are, for example, corn steep liquor, yeast extract, soybean flour, fish meal, skimmed milk powder, partly digested casein or meat extract. So-called "synthetic" nutrient solutions can also be used. It may furthermore be beneficial to add trace elements, such as, for example, zinc, magnesium, iron, cobalt or manganese, to the fermentation medium.

The fermentation which leads to the formation of the W-46 inhibitors can be carried out within a wide temperature range. For example, it is carried out at temperatures between 10° and 40°C., preferably between approximately 20° and 35°C. The pH of the medium is likewise kept at values which are favorable to the growth of the microorganisms, for example at a pH between 4.0 and 10.0, preferably between 6.0 and 9.0. Depending on the nutrient medium, such as, for example, its qualitative and quantitative composition, and the fermentation conditions, such as, for example, the rate of aeration, temperature or pH, the W-46 inhibitors are usually formed in the culture solution after about 1-10 days.

The W-46 inhibitors are found both in the mycelium and in the culture filtrate from the fermentation. Most of the desired W-46 metabolism product is generally to be found in the culture filtrate. The aqueous phase is therefore advantageously separated off from the mycelium, for example by filtration or centrifugation, and the desired product is isolated from the particular phases by processes which are known per se and purified. A large number of processes are suitable for this, such as, for example, chromatography on ion exchangers, molecular sieves or adsorption resins, solvent or salt precipitations, ultrafiltration, Craig partition and the like.

A preferred process for obtaining the components W-46 A, B and C comprises adsorbing the inhibitors from the culture filtrate onto a suitable resin, for example based on polystyrene, separating off this laden resin and isolating the inhibitors mentioned by elution with suitable buffer solutions, such as, for example, phosphate or Na acetate buffer solution, or with organic solvents, if appropriate containing water, such as, for example, methanol, ethanol, acetone or, preferably, aqueous isopropanol. The inhibitor-containing eluates are concentrated by ultrafiltration in a known manner, demineralization simultaneously being carried out. The ion-deficient aqueous solution of the inhibitors mentioned is then separated by chromatography on an ion exchanger column in a manner which is known per se. Strongly or weakly acid cation exchangers, for example based on styrene/divinylbenzene copolymers, which carry —SO$_3$H or —COOH groups as functional groups (®Dowex 50 W or ®Amberlite CG 120), or based on modified sulfopropylcellulose (SP- ®Sephadex), are preferably used as the ion exchanger, but a large number of other commercially available cation exchangers can also be used. The last step of the isolation is the use of molecular sieve, for example based on polyacrylamide gel (®Biogel P-6) or based on modified cellulose (®Sephadex). The resulting aqueous solutions of the pure material are then dried, for example by lyophilization. The specific activity is $4 \times 10^4$ $\alpha$-amylase inhibitor units per mg of solid substance.

Although the substance obtained from the process mentioned is essentially free from impurities, it is not necessarily a single substance chemically. Separation of the products of the individual fermentation batches into biologically active components may be possible by renewed ion exchanger chromatography, for example on SP-Sephadex, molecular sieve chromatography, HPLC separation, for example on reversed phase carrier material containing NH$_2$ groups (®LiChrosorb NH$_2$-carrier) with acetonitrile/water (3:1) mixtures and by similar generally customary processes. The three components which chiefly occur have been given the names $\alpha$-amylase inhibitor W-46 A, W-46 B and W-46 C. Other pseudooligosaccharides with an inhibiting action also occur alongside these compounds.

The pure W-46 inhibitors are colorless, amorphous pseudooligosaccharides. They contain nitrogen and have a weakly basic character. Thus, in high voltage electrophoresis in acid buffers, such as, for example, aqueous formic acid/acetic acid mixtures, the W-46 inhibitors migrate as cations in the direction of the cathode. The substances according to the invention contain glucose in bonded form: acid hydrolysis of the substances gives glucose, alongside, other, usually nitrogen-containing, cleavage products. A further characteristic of the W-46 inhibitors is that they have reducing properties which, as is customary in sugar chemistry, can be demonstrated, for example, with triphenyltetrazolium chloride (TTC).

Several $\alpha$-glucosidase inhibitors with pseudooligosaccharide character have already been described in the literature: E. Truscheit et al., Angew. Chem. 93, pages 738–755 (1981), T. Tajiri et al., Agric. Biol. Chem. 47, pages 671–679 (1983), K. Yokose et al., J. Antibiotics, 36, pages 1157–1175 (1983).

The W-46 inhibitors according to the invention differ from all known $\alpha$-glucosidase inhibitors by the general formula I and also in some cases by the reducing properties, and these are therefore novel substances. They are distinguished by a low polarity and can be obtained microbiologically in good yields.

The properties of the inhibitors according to the invention are of interest in respect of use as a therapeutic against diabetes and prediabetes as well as adiposity and for supplementing the diet. On the basis of their properties, they are also useful as a reagent for diagnostic purposes.

Starch-containing foodstuffs and luxury foods lead to an increase in blood sugar and thereby also to an increased secretion of insulin by the pancreas in animals and humans. Hyperglycemia occurs as a result of breaking down of the starch in the digestive tract to give glucose, under the influence of amylase and maltase.

In diabetics, the hyperglycemia is particularly pronounced and long-lasting.

Both alimentary hyperglycemia and hyperinsulinemia following starch intake can be reduced by the amylase inhibitors according to the invention, in particular by W-46 A, B and C. This effect is dose-dependent. The amylase inhibitors according to the invention can therefore be employed as a therapeutic in cases of diabetes, prediabetes and adiposity and to supplement the diet. For this purpose, oral administration, in particular at mealtimes, is recommended. The dosage should depend on the weight of the patient and the individual requirement and is about 5–500 mg per dose, advantageously taken at each mealtime. However, in individual justified cases, the dosage can also be above or below this amount.

The amylase inhibitors according to the invention are particularly suitable for oral administration. They can be administered as the pure substance, as their physiologically acceptable salts with acids, and also in the form of a pharmaceutical formulation, using the customary auxiliaries and excipients. Combined use with other medicaments, such as hypoglycemic or lipid-lowering substances, may also be advantageous. Since high molecular weight saccharides are not, or not noticeably, absorbed as such from the digestive tract, no toxicologically unacceptable side effects are to be expected of the substances according to the invention. Accordingly, no noteworthy signs were detected following oral administration even of high doses of the W-46 amylase inhibitors to experimental animals. To test the pharmacological action of the amylase inhibitor, fasting male Wistar rats weighing between 200 and 250 g were given an oral administration of a W-46 inhibitor according to the invention or a mixture simultaneously with 2 g of starch per kg of body weight. The efficacy of the product was demonstrated by determining the blood sugar concentrations in blood samples taken before, during and after administration of the $\alpha$-amylase inhibitor. Besides blood glucose regulation, the oligosaccharides according to the invention can also be used for inhibiting salivary $\alpha$-amylase. This enzyme effects digestion of starch in the mouth and the sugar thus formed promotes caries of the teeth. The compounds according to the invention can therefore be used to prevent or reduce the development of caries.

They can furthermore be used as biochemical reagents and as diagnostic agents.

AMYLASE TEST

One amylase inhibitor unit (AIU) is defined as the amount of inhibitor which is capable of inhibiting two amylase units (AU) to the extent of 50% under the test conditions. By international agreement, one amylase unit is the amount of enzyme which cleaves $1\mu$ equivalent of glucosidic bonds in starch in one minute. The $\mu$Eq of glucosidic bonds cleaved are determined photometrically, with dinitrosalicylic, acid as $\mu$Eq of reducing sugars. The data are calculated as $\mu$mol of maltose, determined with the aid of a maltose calibration line.

The tests are carried out as follows:

α-Amylase from the pancreas of pigs and the solutions to be tested are preincubated together in 1.0 ml of 20 mM phosphate buffer, pH 6.9, +10 mM NaCl at 37°C. for 10–20 minutes. The enzymatic reaction is started by addition of 1.0 ml of soluble starch (0.25% strength in the buffer described) according to Zulkowski. After exactly 10 minutes, the reaction is stopped with 2.0 ml of dinitrosalicylic acid color reagent (from Boehringer Mannheim: BiochemicaInformation II) and the mixture is heated in a boiling waterbath for 5 minutes for color development. After cooling, the extinction is measured against the reagent blank value at 546 nm. The 50% inhibition is determined graphically by means of a probability plot in comparison with the non-inhibited enzyme reaction by using various amounts of inhibitor.

EXAMPLE 1

To obtain W-46, the inoculum was cultured (culture of the microorganism)—as is customary in microbiological practice—from a freeze-dried permanent form of the organism *Streptomyces galbus*, FH 1716 DSM 3007, via individual colony passage and with slant tubes. The mass production of spores necessary for the fermentation was likewise carried out on a solid nutrient medium in Roux bottles.

Agar Medium for the Plate, Slant Tube and Roux Bottle

| | |
|---|---|
| Dextrin | 15.0 g/l |
| Sucrose | 3.0 g/l |
| Meat extract | 1.0 g/l |
| Yeast extract | 2.0 g/l |
| Sodium chloride | 0.5 g/l |
| $K_2HPO_4$ | 0.5 g/l |
| $FeSO_4 \times 7 H_2O$ | 0.01 g/l |
| Agar-agar | 2.0 g/l |
| pH | 7.3 |
| Sterilization at 120° C. | 20 minutes |
| Incubation at 30° C. | 9 days. |

The inoculated tube and the Roux bottle were incubated at 30°C. for 7 days and then kept at +4° C. The spores were flushed from the solid nutrient medium with 10 ml of sterilized distilled water or physiological saline solution. 5 ml of the suspension were used to inoculate a 2,000 ml conical flask which had been charged with 500 ml of sterilized aqueous nutrient solution with a pH of 7.7 and with the following composition (data in % by weight).

1.00% of glucose
0.40% of casein peptone
0.40% of meat extract
0.25% of NaCl
0.05% of yeast extract
0.05% of liver powder.

The flask was shaken on a shaking machine at 220 rpm at 30° C. for 48 hours. Thereafter, this preculture was transferred to a 12 liter fermenter which had been charged with 9 liters of sterilized aqueous nutrient solution and in which the pH was 7.4. The composition of the nutrient solution for the main culture was as follows (data in % by weight).

2.0% of meat extract
2.0% of malt extract
1.0% of calcium carbonate
0.1% of antifoam agent
to 100% with water.

The main culture was stirred at 850 rpm at 28° for 2 days, the air supply being 420 liters per hour. The content of α-amylase inhibitor was determined in accordance with the instructions of R. Bender et al., Anal. Biochem. 137, 307–312 (1984) after 18, 24, 30, 36, 40, 44 and 48 hours. Under the experimental and culture conditions desscribed, the strain Str. galbus FH 1716 produced on average $5 \times 10^3$ AIU/ml, at an final pH of 9.0.

EXAMPLE 2

Figure 2:
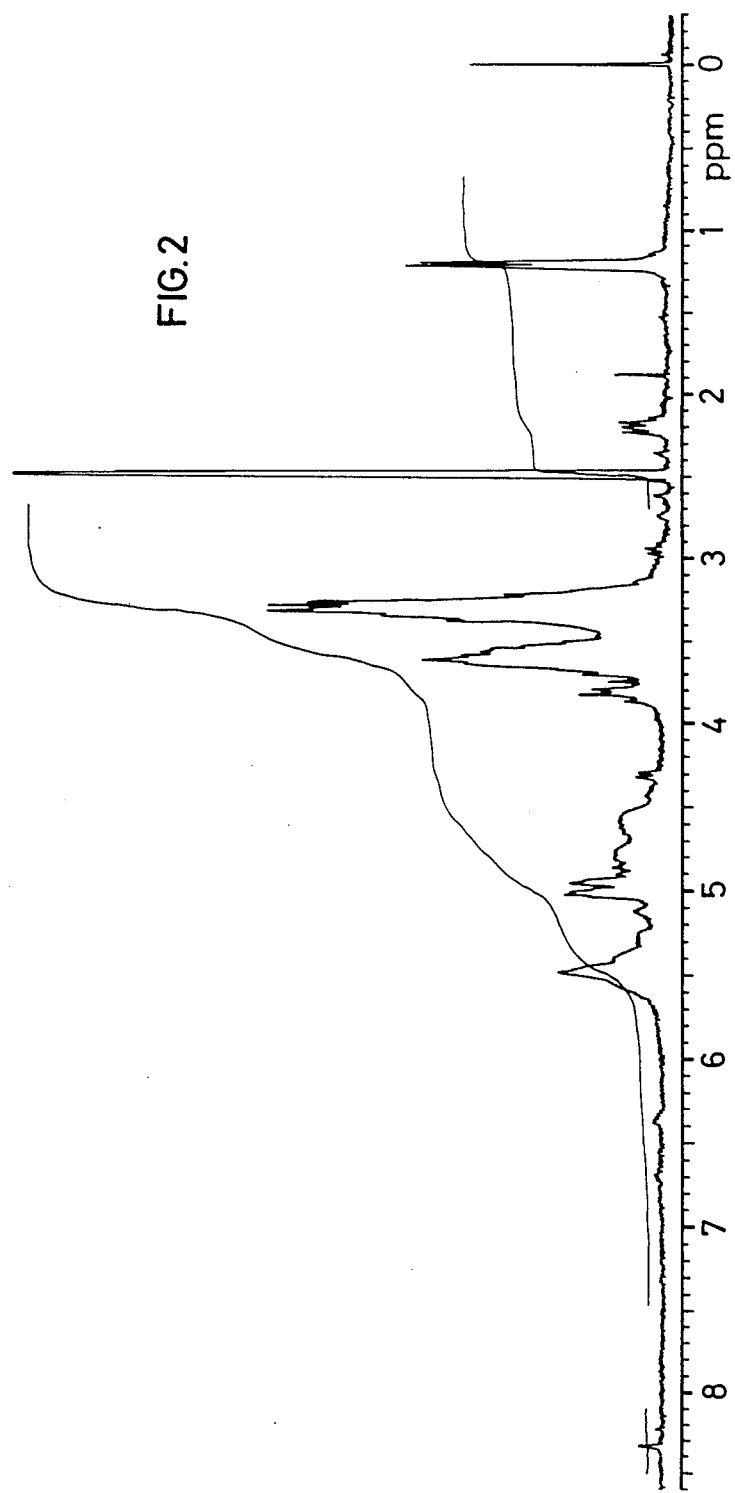

8 liters of fermentation solution according to Example 1 were freed from the cell mass with the aid of a centrifuge and the clear liquid phase was brought to pH 9.5. The solution was then introduced onto a column containing 0.8 liter of polystyrene adsorption resin (Diaion ®HP-20) and the column was rinsed with 1.5 liters of water and eluted with water to which increasing amounts of isopropanol had been added. The mixture which contained 10% of isopropanol detached the W-46 inhibitor from the column. These active eluates (1.2 liters) were concentrated by ultrafiltration and demineralized, with addition of water and with further ultrafiltration, until the retained material no longer contained detectable salts. The resulting concentrate (0.2 liter) was separated on sulfopropyl-modified cellulose (SP-Sephadex ®), which had been converted into the acid form (H+ form). The fractions containing the α-amylase-inhibiting activity were eluted by applying an ammonium acetate gradient, pH 5 (0–0.5 molar). The corresponding fractions were concentrated in ultrafiltration cell (®Amicon) and demineralized. Final purification was effected on polyacrylamide gel (Biogel ®P-6), with pure water as the eluant. The fractions containing W-46 from this column were collected and freeze-dried. 1.5 g of a light beige amorphous powder with an α-amylase-inhibiting activity of $4 \times 10^4$ AIU per mg of substance resulted. The IR spectrum (in KBr) is shown in FIG. 1 and the NMR spectrum (in DMSO) is given in FIG. 2.

EXAMPLE 3

100 mg of the W-46 inhibitor mixture obtained according to Example 2 were dissolved in 0.01% phosphate buffer, pH 7.8, and separated on 150 g of Li-Chrosorb RP 18 carrier in a steel column under HPLC conditions. 95% of 0.01% strength phosphate buffer, pH 7.8, with 5% of acetonitrile was used here as the eluting agent and detection of the eluate was carried out by UV absorption measurement at 210 nm. After 4, 5.8 and 7.5 minutes, material with an inhibiting action was obtained by separation from the column. These fractions were concentrated, demineralized and freeze-dried. Their analysis showed:

Peak I (after 4 minutes of HPLC); C: 45.8%, H: 6.4%, N: 1.9%, O: 46.0%. An M +H+ peak of 1,467 was found by FAB mass spectrometry (W-46 C).

Peak II (after 5.8 minutes of HPLC); C: 46.1%, H: 6.5%, N: 2.1%, O: 45.4%. FAB mass spectrometry (FAB-MS), M+H+ peak: 1,305 (W-46 B)

Peak III (after 7.5 minutes of HPLC); C: 46.3%, H: 6.5%, N: 2.5%, O: 44.8%. FAB-MS, M+H+ peak: 1,143 (W-46 A).

EXAMPLE 4

100 mg of the material obtained according to Example 2 were dissolved in 0.5 ml of water, the solution was brought to pH 1 at 0° C. with hydrochloric acid, and 5 ml of acetone were added. The resulting precipitate was collected by centrifugation and taken up in water and the mixture was freeze-dried. The hydrochloride of the W-46 inhibitor mixture was obtained.

EXAMPLE 5

Changes in the increase in blood glucose of starch-laden rats as a function of the orally administered dose of the W-46 inhibitor mixture.

Method:

The experimental animals were 45 male Albino rats. The animals had no access to food 18 hours before and during the experiment. In each case 8–10 animals received an oral administration of 0.3, 0.6 and 1.0 mg/kg W-46 inhibitor according to Example 2 together with 2 g/kg starch, suspended in tapwater, by means of a stomach tube. The administration volume was 1 mg/100 g of body weight. 18 control animals received only starch suspension. In each case 10 μl of blood were sampled immediately before and 0.5, 1, 2, 3 and 5 hours after the treatment and the blood glucose was determined enzymatically.

Results:

The W-46 inhibitor mixture caused a dose-dependent reduction in the postprandial increase in blood glucose following starch loading. 1 hour after the treatment, 0.3, 0.6 and 1 mg/kg of W-46 inhibitor effected at least a 16, 23 and 25% reduction in the increase in blood sugar in comparison with the control values. The dose-dependency is statistically confirmed. The limit value of the dose for the average percentage increase in blood glucose over 3 hours is 0.4 mg/kg.

We claim:

1. A pseudooligosaccharide of the formula I

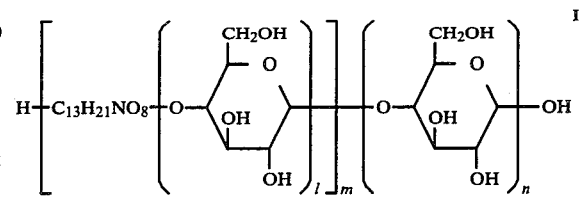

in which
l=1 or 2
m=1, 2 or 3 and
n denotes an integer from 1 to 20
and a physiologically acceptable salt thereof with an acid.

2. A psuedooligosaccharide as claimed in claim 1, in which, in formula I, 1 denotes 1, m denotes 1 or 2 and n denotes 1, 2, 3 or 4.

3. A pharmaceutical product for the treatment of diabetes, prediabetes and adiposity containing an effective amount of a pseudooligosaccharide as claimed in claim 1, and a pharmaceutically acceptable carrier.

4. A pharmaceutical product for the treatment of diabetes, prediabetes and adiposity containing an effective amount of a pseudooligosaccharide of the formula I as recited in claim 1 in which the letter l denotes the number 1, m denotes 1 or 2 and n denotes 1, 2, 3 or 4, and a pharmaceutically acceptable carrier.

5. A method which comprises using a pseudooligosaccharide as claimed in claim 1 for inhibition of α-glucosidase.

6. A method for the treatment of diabetes, prediabetes and adiposity, wherein an effective amount of a compound as claimed in claim 1 is administered.

7. A method which comprises using a pseudooligosaccharide as claimed in claim 1 as a diagnostic aid, reagent or prophylactic against caries.

* * * * *